US00PP23210P3

(12) United States Plant Patent
Kurashima et al.

(10) Patent No.: US PP23,210 P3
(45) Date of Patent: Nov. 20, 2012

(54) MUSHROOM NAMED 'PLE-3'

(50) Latin Name: *Pleurotus eryngii*
Varietal Denomination: PLE-3

(75) Inventors: Eriko Kurashima, Nagano (JP); Satoshi Inatomi, Nagano (JP)

(73) Assignee: Hokuto Corporation, Nagano (JP)

( * ) Notice: Subject to any disclaimer, the term of this patent is extended or adjusted under 35 U.S.C. 154(b) by 33 days.

(21) Appl. No.: 12/585,095

(22) Filed: Sep. 3, 2009

(65) Prior Publication Data

US 2011/0055990 P1 Mar. 3, 2011

(30) Foreign Application Priority Data

Sep. 5, 2008 (JP) ..... 2008-022929
Sep. 20, 2008 (JP) ..... 2008-022928

(51) Int. Cl.
*A01H 15/00* (2006.01)

(52) U.S. Cl. ..... Plt./394

(58) Field of Classification Search ..... Plt./394
See application file for complete search history.

*Primary Examiner* — June Hwu
(74) *Attorney, Agent, or Firm* — Wenderoth, Lind & Ponack, L.L.P.

(57) ABSTRACT

The present invention relates to new, distinct horticultural varieties of mushroom plant of the species *Pleurotus eryngii*. The new varieties, named 'PLE-3', was found by crossbreeding *eryngii* varieties having dominant traits. The varieties are featured by its presentable carpophore, delicacy, stability and uniformity and pronounced distinguishability.

10 Drawing Sheets

VARIETAL DENOMINATION

Latin name of the genus and species of the plant claimed: *Pleurotus Eryngii*.

Variety denomination: *Eryngii 'PLE-*3'.

BACKGROUND OF THE INVENTION

The present invention relates to a new and distinct cultivar of mushroom plant of the species *Pleurotus eryngii*. Particularly, this invention relates to a new cultivar of *eryngii*, which is produced by crossbreeding *eryngii* varieties having dominant traits and featured by its presentable carpophore, delicacy, stability and uniformity and pronounced distinguishability.

Bottle cultivation has started around 1993 in Japan to produce the *eryngii*. In 2008, 38000 tons of *eryngii* was produced in Japan. The *eryngii* grows wild in North America, but it has been sparsely cultivated by a cultivation method using a bag and is in slight demand as food. Recently, bottle cultivation for producing the *eryngii* on a factory scale has started. Since it has been learned that the *eryngii* is low in calories and has beneficial effects of preventing fatty liver, future increase in demand for *eryngii* is expected.

However, the modern cultivar of *eryngii* is good in quality, but it has little adaptability to cultivation conditions such as a culture medium type in the U.S. As an example, a cultivating cycle are somewhat lengthened, thus posing a problem to industrial yieldability.

SUMMARY OF THE INVENTION

In view of the foregoing disadvantages inherent in the known types of *eryngii* now present in the prior art, for the purpose of solving problems in cultivating the modern cultivar of *eryngii* and preserving the quality as well or better than the modern cultivar, the present invention provides mushroom named 'PLE-3' cultivated and produced by crossbreeding parent strains 'HOKUTO PLE-2' and 'MH006376' having superior properties of stability, uniformity and distinguishability.

The successfully cultivated mushroom named 'PLE-3' of the invention is the same strain created by crossbreeding the same parents, so to speak, brothers.

DETAILED DESCRIPTION OF THE INVENTION

The present invention relates to a new and distinct cultivar of mushroom named 'PLE-3' belonging to *Pleurotus eryngii*, featured by its presentable carpophore, delicacy, stable and consistent productivity and pronounced distinguishability. The mushroom 'PLE-3' of the invention are cultivated in the following cultivation processes.

PROCESSES OF CULTIVATION

July 2004: Strain MH006367 having dominant trait was produced by crossbreeding parent strains HOKUTO PLE-2 and MH006220.

February 2007: Strain MH006376 was produced by crossbreeding an existing strain MH006322 and the aforementioned strain MH006367.

December 2007: Variety PLE-3 was produced by crossbreeding the aforementioned HOKUTO PLE-2 and MH006376, and then, a cultivation experiment and a characteristic assay were made about the variety PLE-3 thus obtained.

August 2008: The cultivation of PLE-3 was concluded after confirmation of distinguishability, stability and uniformity of the strains.

September 2008: With respect to the new variety PLE-3, applications for plant variety registration were filed with Agriculture, Forestry and Fisheries Ministry of Japan and accepted on 5 Sep. 2008.

The place where PLE-3 was asexually reproduced is Mushroom Multidiscipline Laboratory of Hokuto Corporation of 800-8, Shimokomazawa, Nagano-shi, Nagano, Japan.

The asexual reproduction was via 'successive subculture' or 'subculture', that is, a method in which the strain is repeatedly subcultured.

CHARACTERISTICS OF PLE-3

(1) Feature Comparison with Existing Varities

Figure 1A:
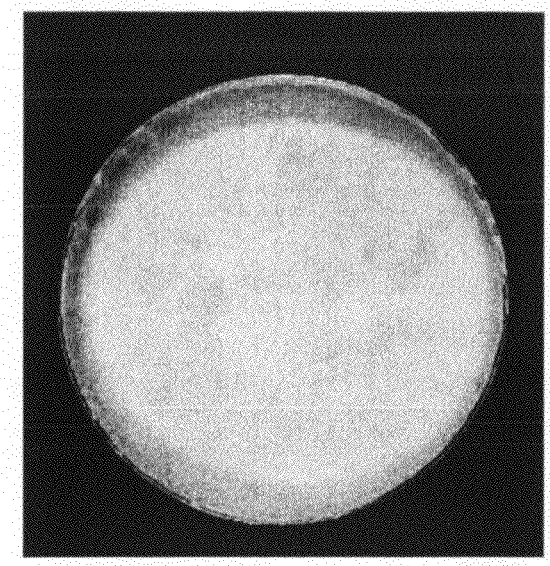
FIGS. 1(A) and 1(B) are photographs showing the top and bottom of dual culture of two 'PLE-3' strains of the invention.
Figure 1B:
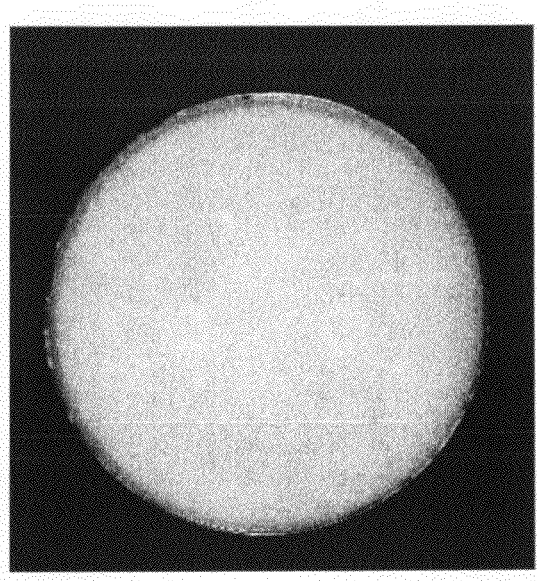
Figure 2A:
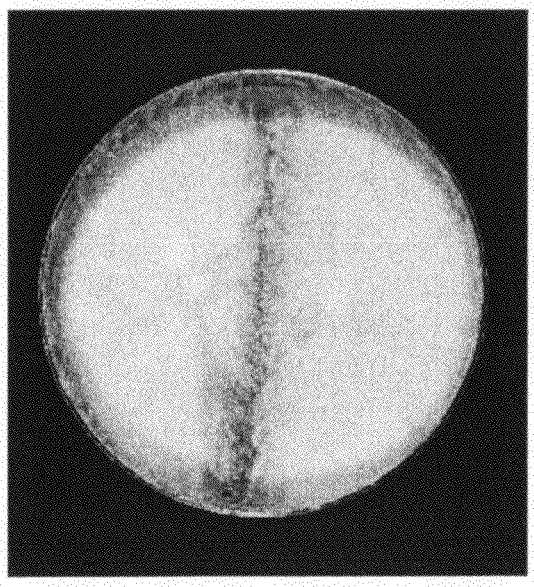
FIGS. 2(A) and 2(B) are photographs showing the top and bottom of dual culture of 'PLE-3' strain of the invention and parent strain 'HOKUTO PLE-2'.
Figure 2B:
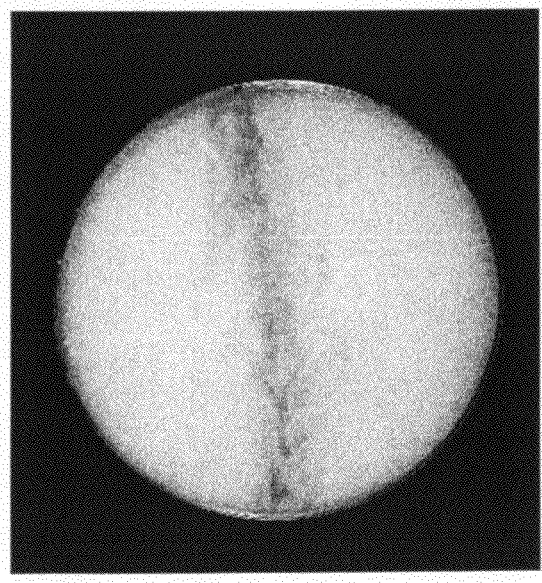
Figure 3A:
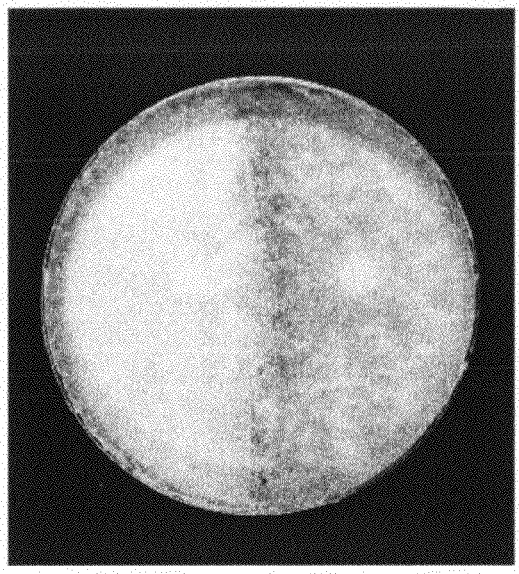
FIGS. 3(A) and 3(B) are photographs showing the top and bottom of dual culture of 'PLE-3' strain of the invention and strain 'ATCC32047'.
Figure 3B:
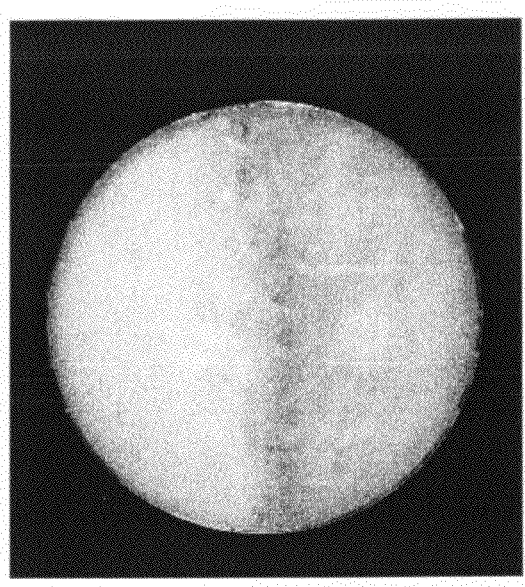
Figure 4A:
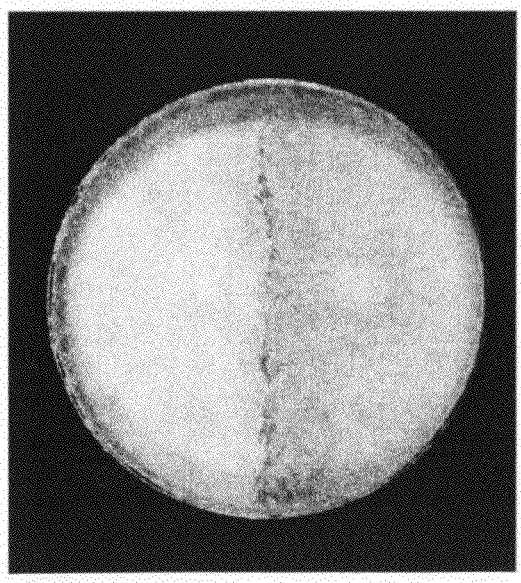
FIGS. 4(A) and 4(B) are photographs showing the top and bottom of dual culture of 'PLE-3' strain of the invention and strain 'ATCC90212'.
Figure 4B:
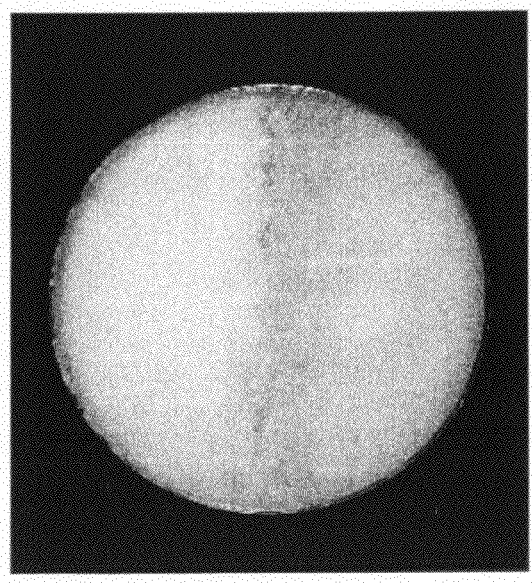
Figure 5A:
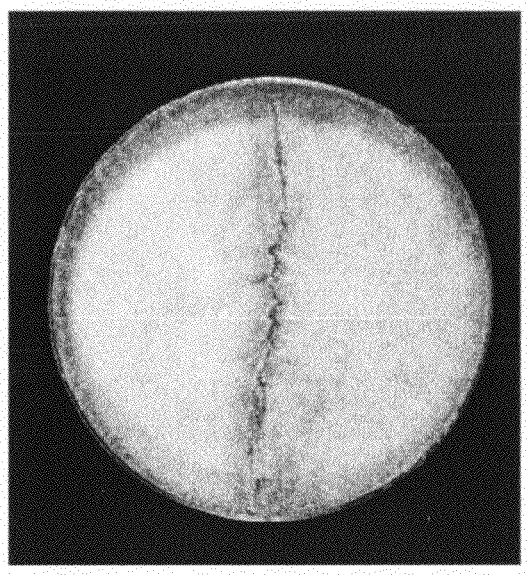
FIGS. 5(A) and 5(B) are photographs showing the top and bottom of dual culture of 'PLE-3' strain of the invention and strain 'ATCC90787'.
Figure 5B:
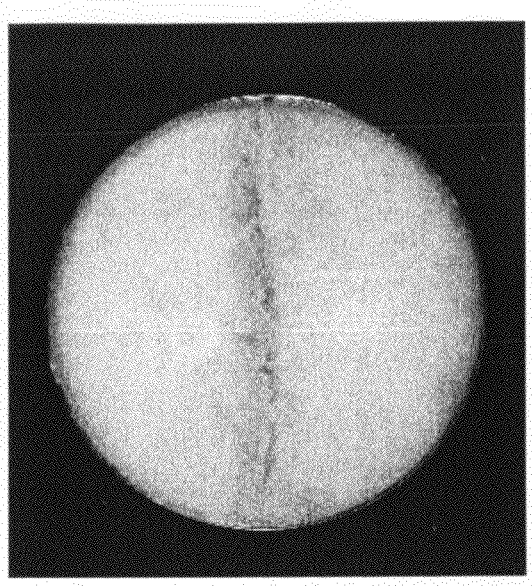
Figure 6A:
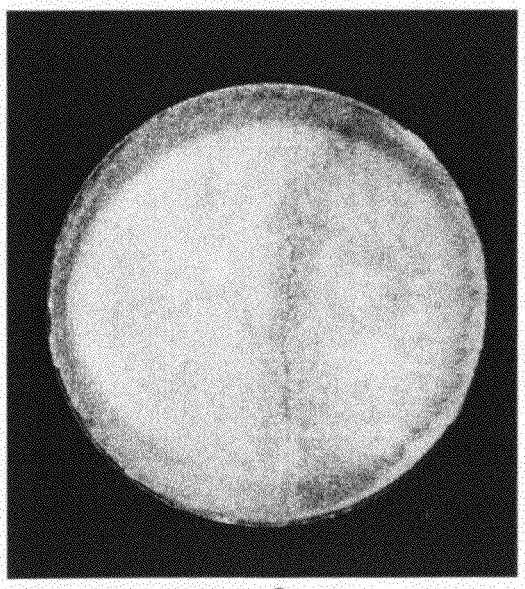
FIGS. 6(A) and 6(B) are photographs showing the top and bottom of dual culture of 'PLE-3' strain of the invention and strain 'ATCC90887'.
Figure 6B:
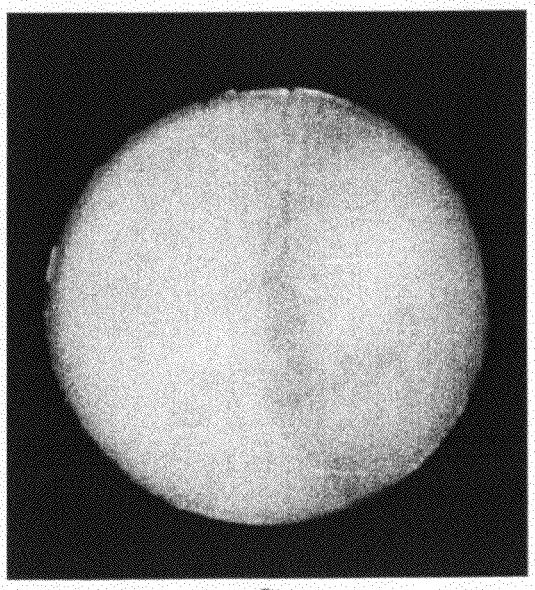
Figure 7A:
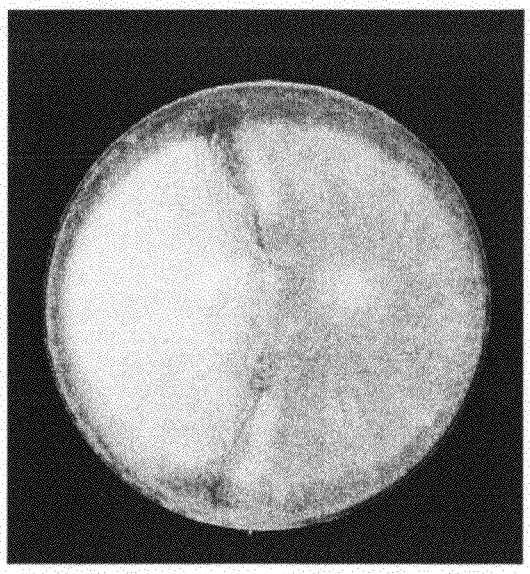
FIGS. 7(A) and 7(B) are photographs showing the top and bottom of dual culture of 'PLE-3' strain of the invention and strain 'ATCC90888'.
Figure 7B:
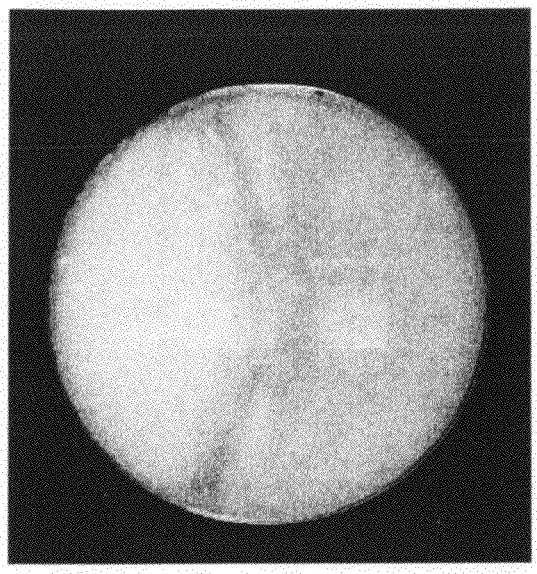
Figure 8A:
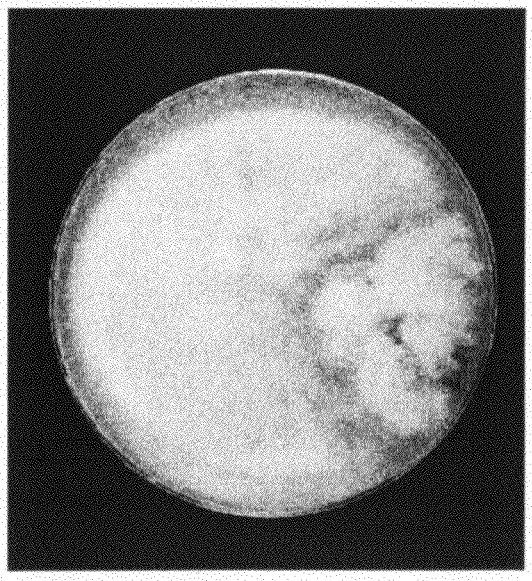
FIGS. 8(A) and 8(B) are photographs showing the top and bottom of dual culture of 'PLE-3' strain of the invention and strain 'ATCC96054'.
Figure 8B:
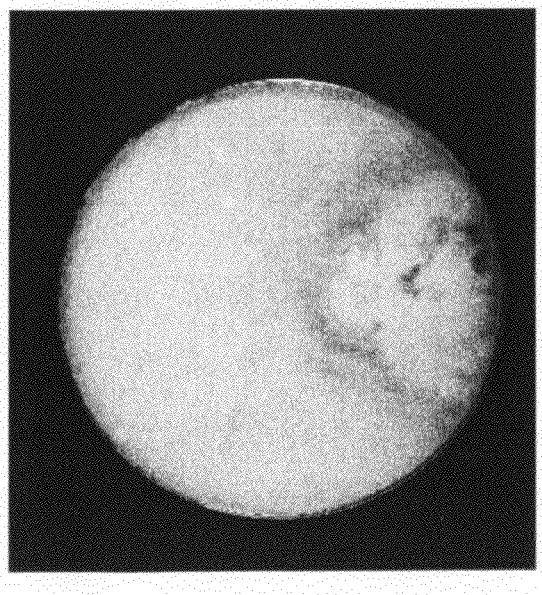
Figure 9A:
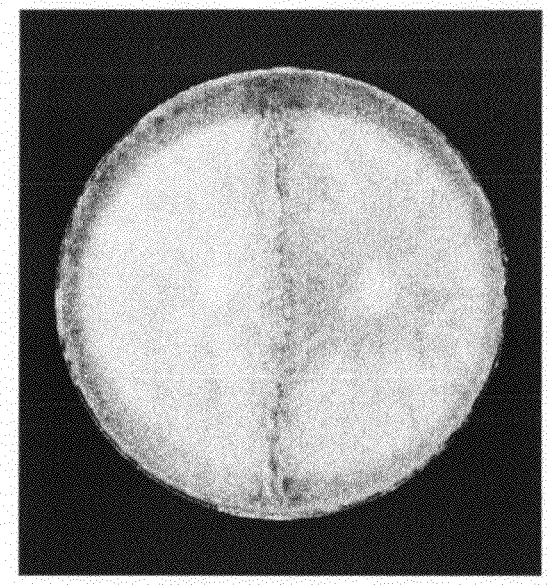
FIGS. 9(A) and 9(B) are photographs showing the top and bottom of dual culture of 'PLE-3' strain of the invention and strain 'MH006062'.
Figure 9B:
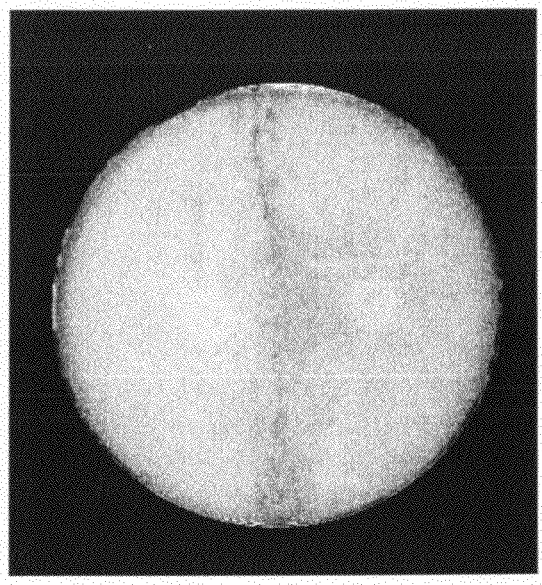
Figure 10A:
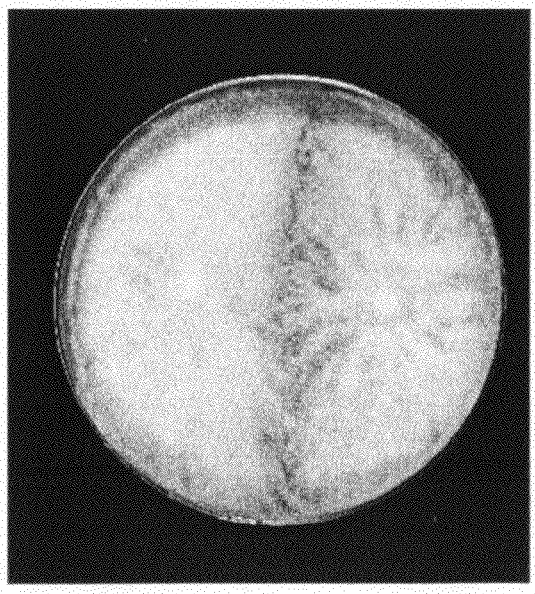
FIGS. 10(A) and 10(B) are photographs showing the top and bottom of dual culture of 'PLE-3' strain of the invention and strain 'MH006200'.
Figure 10B:
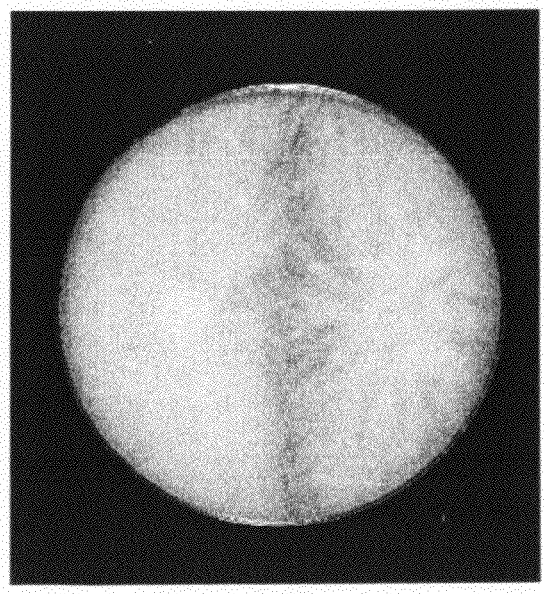
Figure 11A:
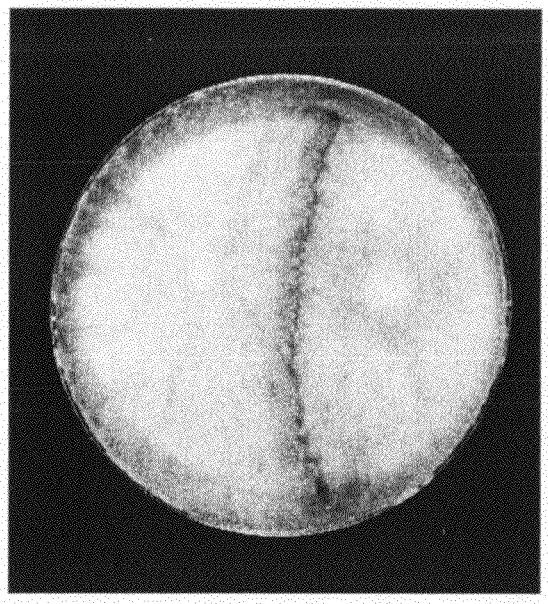
FIGS. 11(A) and 11(B) are photographs showing the top and bottom of dual culture of 'PLE-3' strain of the invention and strain 'MH006202'.
Figure 11B:
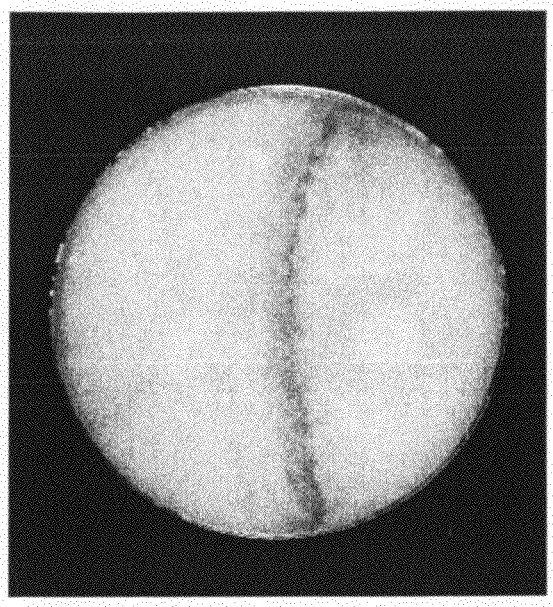
Figure 12A:
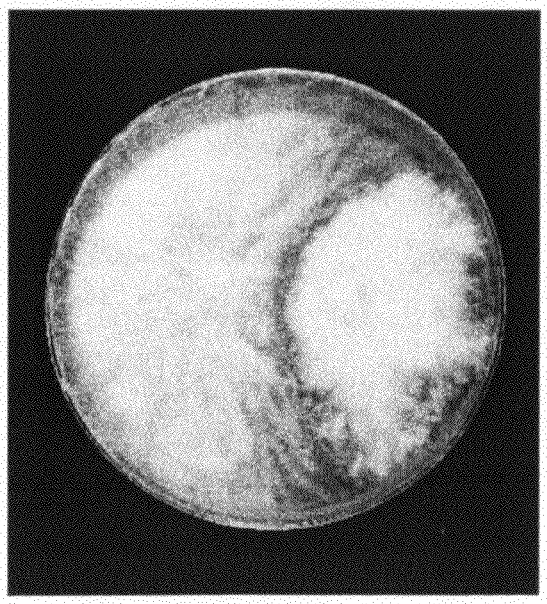
FIGS. 12(A) and 12(B) are photographs showing the top and bottom of dual culture of 'PLE-3' strain of the invention and strain 'MH006207'.
Figure 12B:
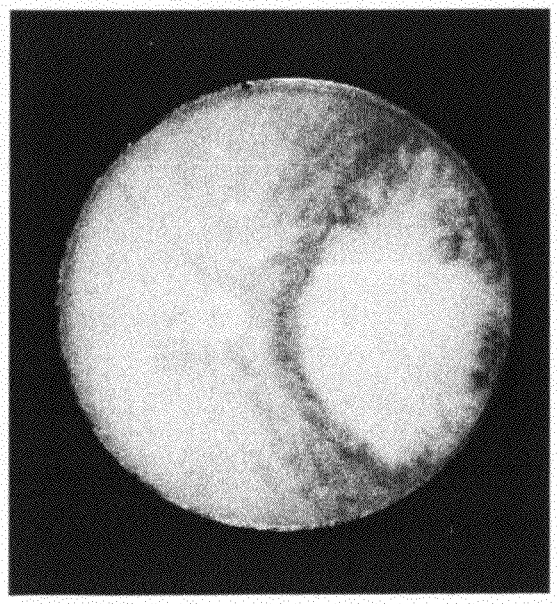
Figure 13A:
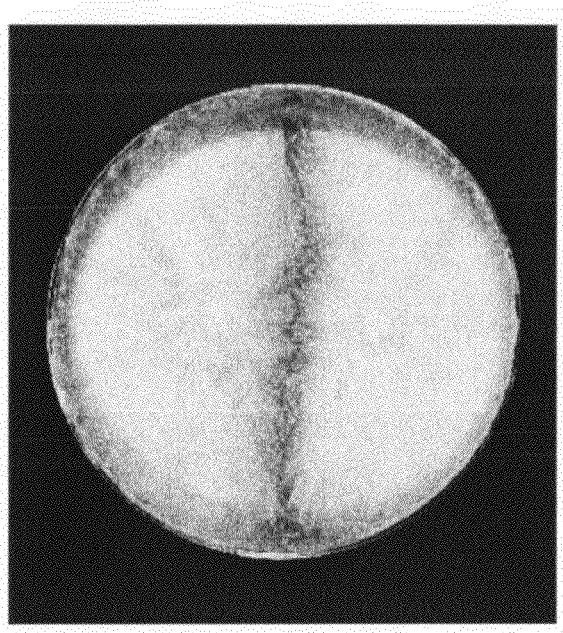
FIGS. 13(A) and 13(B) are photographs showing the top and bottom of dual culture of 'PLE-3' strain of the invention and strain 'MH006322'.
Figure 13B:
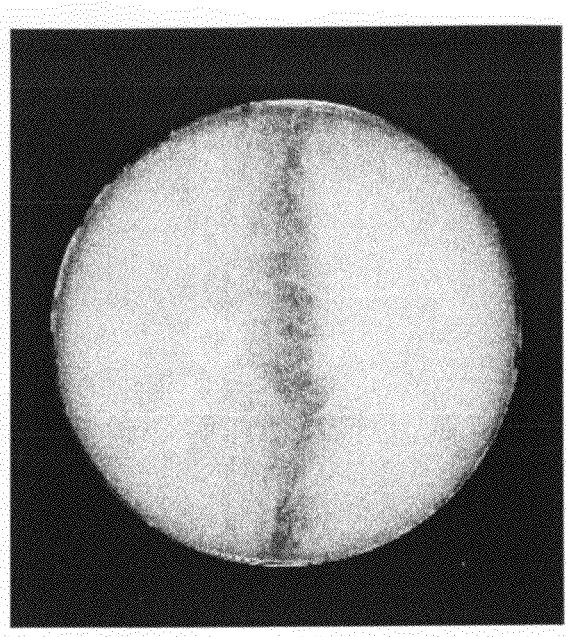
Figure 14A:
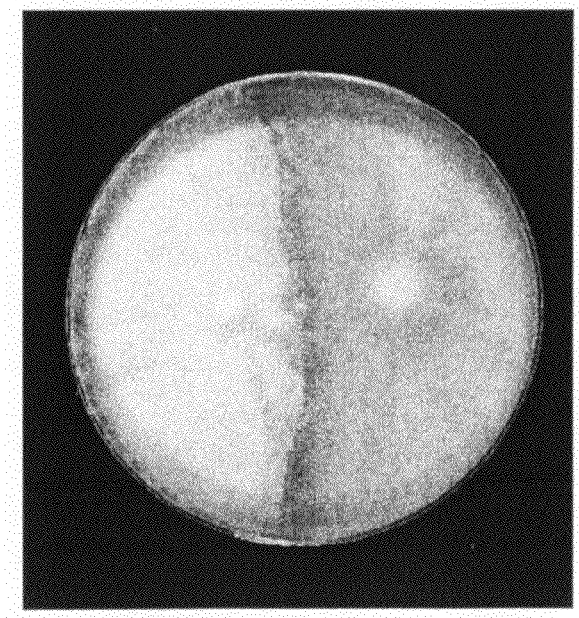
FIGS. 14(A) and 14(B) are photographs showing the top and bottom of dual culture of 'PLE-3' strain of the invention and strain 'MH006219'.
Figure 14B:
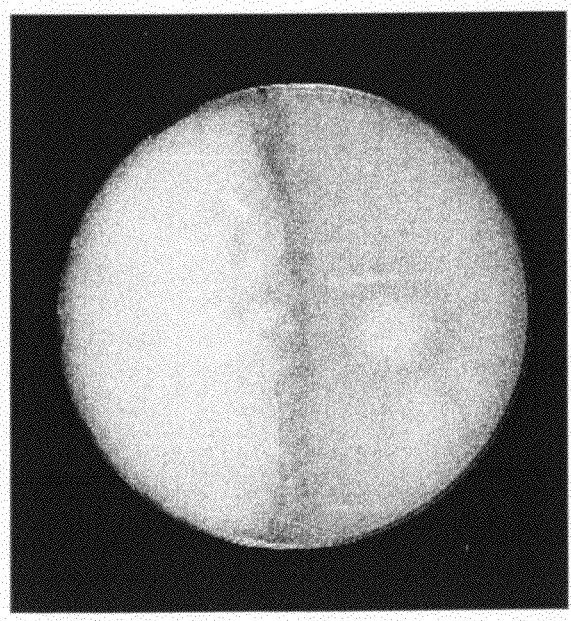
Figure 15A:
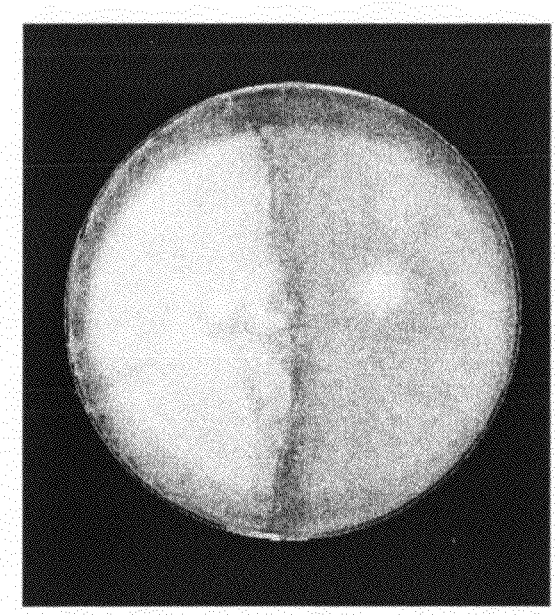
FIGS. 15(A) and 15(B) are photographs showing the top and bottom of dual culture of 'PLE-3' strain of the invention and strain 'MH006242'.
Figure 15B:
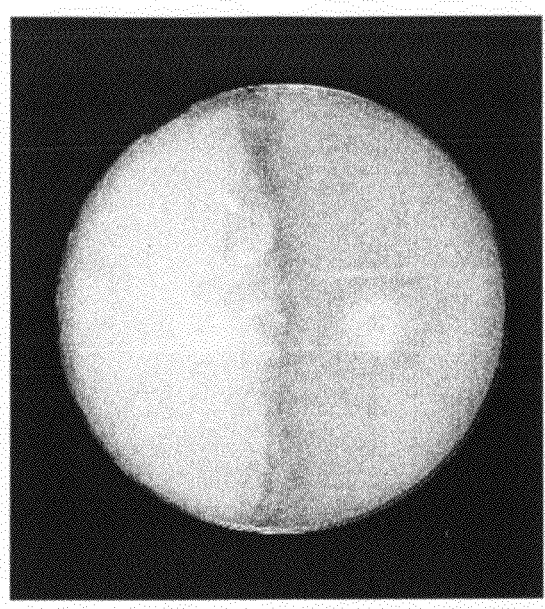
Figure 16A:
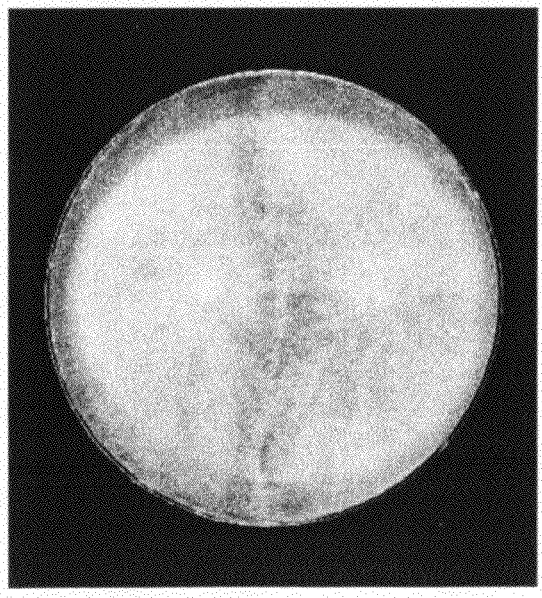
FIGS. 16(A) and 16(B) are photographs showing the top and bottom of dual culture of 'PLE-3' strain of the invention and strain 'MH006279'.
Figure 16B:
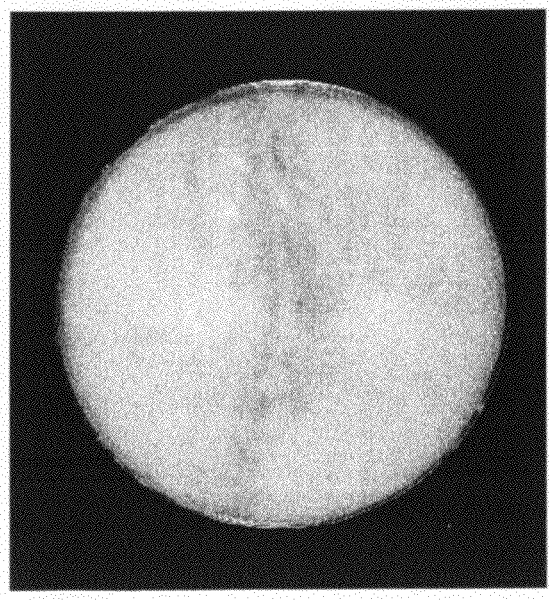
Figure 17:
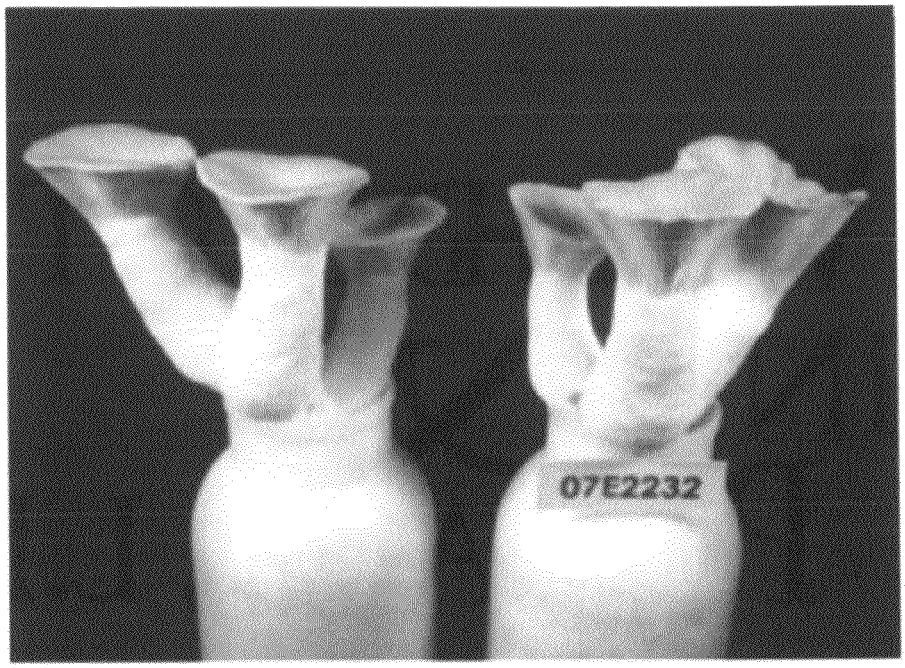
FIG. 17 is a photograph showing carpophore of 'PLE-3' strain of the invention in a culturing state in a characteristic assay.
Figure 18:
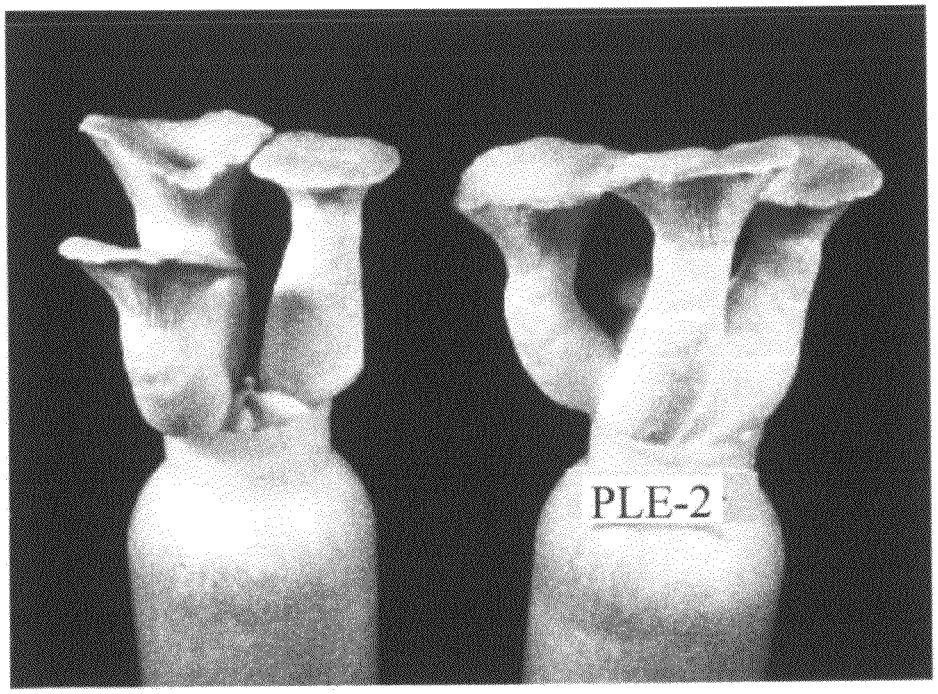
FIG. 18 is a photograph showing carpophore of parent strain 'HOKUTO PLE-2' in a culturing state in a characteristic assay.

To briefly confirm a genetical new kind of variety, a method for investigating a reluctant reaction in a dual culture can be applied. That is, this method can clarify genetic difference of the new variety from the existing by observing the reluctant reaction in the dual culture. Consequently, PLE-3 of the invention could be identified as new varieties by the dual culture method using the existing varieties (FIGS. 1(A) and 1(B)).

[Verification Method]

To verify the reluctant reaction, the dual culture was prepared by placing fungal strains on potato dextrose agar medium at intervals of 3 cm in juxtaposition and cultivating the strains at 25 degrees C. for 28 days. The fungal strains used in the reluctant reaction experiment in the dual culture are shown in Table 1 below.

TABLE 1

Fungal strains used in the reluctant reaction experiment

| No. | Strain Name |
|---|---|
| — | HOKUTO PLE-2 |
| 07E2232 | PLE-3 |
| 1 | ATCC32047 |
| 2 | ATCC90212 |
| 3 | ATCC90787 |
| 4 | ATCC90887 |
| 5 | ATCC90888 |
| 6 | ATCC96054 |
| 7 | MH006062 (commercial strain: Fujita's Eryngii) |
| 8 | MH006200 (commercial strain: JA Fukuoka) |
| 9 | MH006202 (commercial strain: Yukiguni Maitake) |
| 10 | MH006207 (commercial strain: Masuda-Kashiwagi Mushroom) |
| 11 | MH006322 (commercial strain: Chokin-15) |
| 12 | MH006219 (commercial strain: Wild strain #1 grown in Italy) |
| 13 | MH006242 (commercial strain: Wild strain #2 grown in Italy) |
| 14 | MH006279 (commercial strain: Wild strain #1 grown in Spain) |

[Results:]

The results of the reluctant reaction experiment are shown in Table 2. In Table 2, the mark "+" denotes occurrence of reluctant reaction, and the mark "–" denotes no reluctant reaction.

All strains other than PLE-3 showed reluctant reaction relative to PLE-3 (07E2232) of the invention.

TABLE 2

Results of dual culture

| Strain No. | PLE-3 |
|---|---|
| 07E2232 (PLE-3) | – |
| HOKUTO PLE-2 | + |
| 1 (ATCC32047) | + |
| 2 (ATCC90212) | + |
| 3 (ATCC90787) | + |
| 4 (ATCC90887) | + |
| 5 (ATCC90888) | + |
| 6 (ATCC96054) | + |
| 7 (MH006062) | + |
| 8 (MH006200) | + |
| 9 (MH006202) | + |
| 10 (MH006207) | + |

TABLE 2-continued

| Results of dual culture | |
|---|---|
| Strain No. | PLE-3 |
| 11 (MH006322) | + |
| 12 (MH006219) | + |
| 13 (MH006242) | + |
| 14 (MH006279) | + |

+: Reluctant reaction occurred
−: No reluctant reaction occurred (2) Cultural Characteristics of PLE-3

The strain PLE-3 of the invention was cultivated on the potato dextrose agar medium to be investigated in mycelial characteristics and so on. Consequently, the mycelia of all of the strains energetically grew. The growing rate of the mycelia at 20 degrees C. was about 3 mm a day (colony diameter). The strain having a flora surface of white (RHS: NN155C) could be obtained.

(3) Morphologically Characteristics of PLE-3

[Cultivation Method] (Examination Standard for *Eryngii* prescribed for plant variety registration based on Japanese Seeds and Seedlings Law was adopted.)

Bottle cultivation was performed using a polypropylene bottle having a bore diameter of 58 mm and a capacity of 850 ml. A culture medium was prepared by mixing cedar sawdust, bran and corn bran at the mixture ratio of 10:3:0.5 and regulating the water content to 65%. The cultivating bottle was filled up to the bottle shoulder with 510±10 grams of the culture media, and then, sterilized at high pressure. After the culture medium cooled, about 15 ml of sawdust seed fungus was implanted in the culture medium. The culture medium was controlled at 23 degrees C. and at a humidity of about 70%.

The culture medium was subjected to fungus scratching treatment after being cultivated for 40 days, and then, moved to an emergence room without dilution by water. The emergence room was controlled at a temperature of 17±1 degrees C., a humidity of 90%, an illumination intensity of 200 LUX and $CO_2$ concentration of approximately 2000 ppm. Mushrooms thus grown were harvested three days after the mushroom cap at the center of the carpophore spreads horizontally. The carpophore thus harvested was observed to determine the shape of its pileus. The results of verification based on Examination standard for *Eryngii* prescribed for plant variety registration based on Japanese Seeds and Seedlings Law will be described below.

[Results]

Morphological Characteristics of PLE-3

The pileus of PLE-3 has a concave shape. There was a sharp difference in that PLE-3 has a thickness of 15.38 mm. With respect to the shape of hymenophorum, PLE-3 has a mushroom stem moderately attached to the pileus. The pileus assumes an "emarginatd" shape, i.e. is shaped in "upturn". The mushroom stem of PLE-3 has a relatively thick lower part. The mushroom stem of PLE-3 is 79.41 mm in length. The mushroom stem of PLE-3 is 26.7 mm in diameter. With respect to the other features than those noted above, PLE-3 has 3.14 carpophore stems on an effective average. The gill attachment of 'PLE-3' is essentially subdecurrent. The characteristic values of the mushrooms 'PLE-3' shown in Table 3 express the attaching intensity of the subdecurrent to the stem. The attaching intensity of the subdecurrent to the stem of the mushroom 'PLE-3' is "moderate" as shown in the table.

These characteristic features of PLE-3 are shown in Table 3 below. The distinctions between the new variety of the invention and the parent varieties "PLE-2" and "MH006376" are apparent from Table 3. MH006376 is an intermediate variety derived from the process of growing PLE-3, i.e., the variety obtained through mating experiments carried out in the laboratory. That is, the variety of PLE-3 and MH006376 are different in that the growing of the variety of PLE-3 has been completed, but the growing of MH006376 was insufficient. Furthermore, MH006376 having a small yielding ability (90.2 grams) and a small number of stems (two or three stems) is further distinguished from the variety of the present invention.

TABLE 3

| Characteristic Features of PLE-3 (Characteristics of PLE-3 and characteristics of commercial similar variety HOKUTO PLE-2) Investigation place: Mushroom Laboratory, Hokuto Corporation of Shimokomazawa, Nagano-shi, Nagano, Japan Investigation Period: 1st May, 2008 to 20th August, 2008 | | |
|---|---|---|
| Trait | PLE-3 | HOKUTO PLE-2 |
| (1) Fungal Property | | |
| Fungal density | Medium | Medium |
| Growth status of aerial mycelia | Normal | Normal |
| Peripheral shape of flora | Concentric | Concentric |
| Color of upper surface of flora | White (RHS: N155C) | White (RHS: N155C) |
| Color of lower surface of flora | Cream (RHS: 11D) | Cream (RHS: 11D) |
| (2) Temperature Adaptability | | |
| Optimum temperature of mycelial growth (° C.) | 27 | 28 |
| Growth rate at respective temperatures (mm/day) | | |
| 5° C. | 0.45 | 0.35 |
| 10° C. | 1.18 | 1.46 |
| 15° C. | 1.8 | 1.96 |
| 20° C. | 2.95 | 3.73 |
| 25° C. | 6.04 | 6.05 |
| 30° C. | 5.22 | 5.96 |
| (3) Morphological Features | | |
| Pileus | | |
| Shape | Concave | Flat |
| Pattern | Streaky | Streaky |
| Surfice protrusion | None | None |
| Size (mm) | 51.01 | 54.89 |
| Color of center part | (RHS: 199D) | (RHS: 199D) |
| Color of periphery | (RHS: 199D) | (RHS: 199D) |
| Thickness (mm) | 15.38 | 15.51 |
| Tenderness | Tough | Tough |
| Hymenophorum | | |
| Alignment | Linear | Linear |
| Attaching intensity to stem | Moderate | Moderate |
| Width (mm) | 3.17 | 3.07 |
| Color | (RHS: 161D) | (RHS: 161D) |
| Stem | | |
| Shape | Thick lower part | Thick lower part |
| Attaching to pileus | Center part | Center part |
| Length (mm) | 79.41 | 86.87 |
| Ratio of pileus diameter to stem length | 0.66 | 0.64 |
| Diameter (mm) | 26.7 | 28.04 |
| Color | Pale yellow (RHS: 158D) | Pale yellow (RHS: 158D) |

TABLE 3-continued

Characteristic Features of PLE-3
(Characteristics of PLE-3 and characteristics of commercial similar variety HOKUTO PLE-2)
Investigation place: Mushroom Laboratory, Hokuto Corporation of Shimokomazawa, Nagano-shi, Nagano, Japan
Investigation Period: 1st May, 2008 to 20th August, 2008

| Trait | PLE-3 | HOKUTO PLE-2 |
|---|---|---|
| Tenderness | Tough | Tough |
| Growing development figure of carpophore | | |
| Development figure | Monogenic | Monogenic |
| Effective stem number | 3.14 | 3.07 |
| Period up to development peak (day) | 64.15 | 64.71 |
| Period from fungus scratching to development (day) | 24.15 | 24.71 |
| Temperature Adaptability | | |
| Optimum temperature of development (° C.) | 17 | 17 |
| Optimum temperature of growing (° C.) | 17 | 17 |
| Yield (g) | 134.23 | 121.1 |

*"RHS" in the items related to color is short for Royal Horticultural Society, and the color codes found above are referred to the color charts stipulated by RHS (Fifth Edition, 2007).

Figure 19:
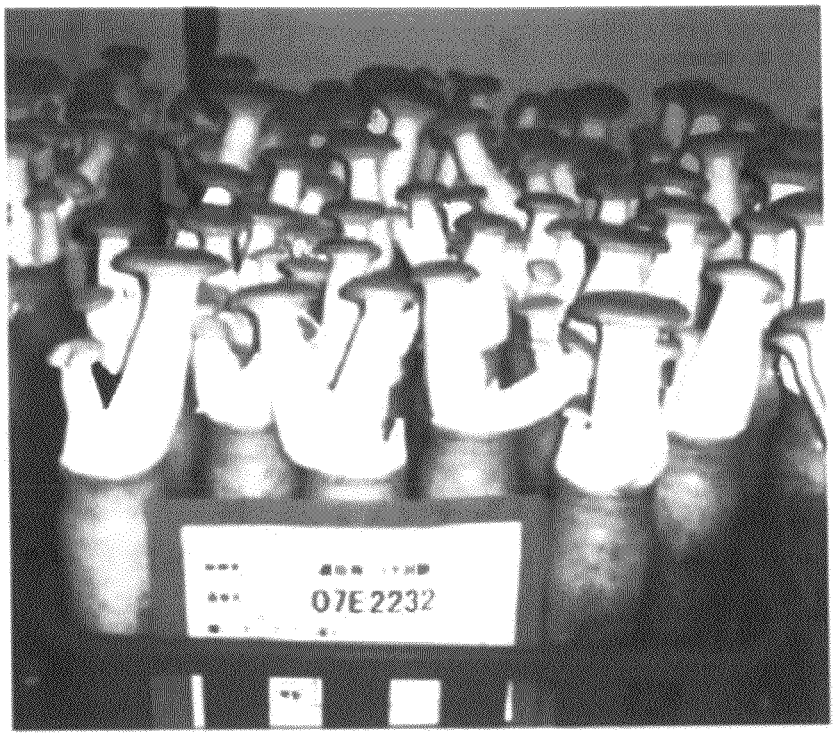
FIG. 19 is a photograph showing carpophore of 'PLE-3' strain of the invention under normal cultivation.
Figure 20:
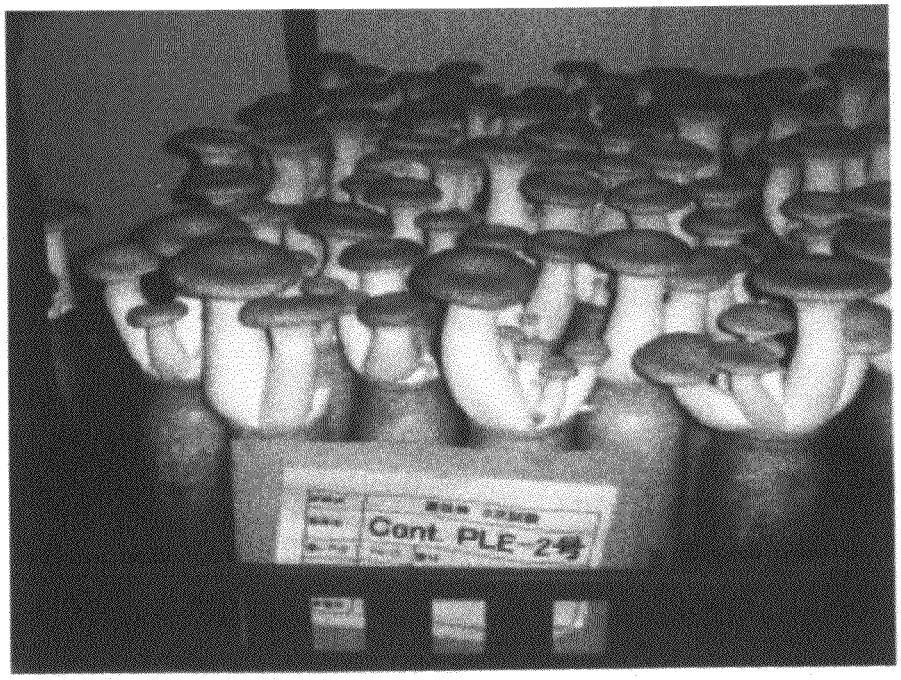
FIG. 20 is a photograph showing carpophore of parent strain 'HOKUTO PLE-2' under normal cultivation.

(4) Embodiments in Case of Cultivation in a Culture Medium for Commercial Production The culture media prescribed as above were used herein to evaluate the varieties cultivated according to the invention and identify the morphological features of the varieties, but the culture media applicable for cultivating the object varieties have been improved to increase productivity of the subject mushrooms in an actual commercial production. Accordingly, the quality of the mushrooms actually produced may possibly not be consistent with the resultant data obtained from the cultivation experiment as described above. Thus, the mushrooms produced commercially in actuality according to the invention are demonstrated in FIGS. 19 and 20.

What is claimed is:

1. A new and distinct variety of mushroom as substantially illustrated or described in the specification.

* * * * *